(12) United States Patent
Hagiya

(10) Patent No.: US 8,071,805 B2
(45) Date of Patent: Dec. 6, 2011

(54) PROCESS FOR PRODUCING 2-HYDROXY-4-(METHLTHIO)BUTYRATE COMPOUNDS AND INTERMEDIATES THEREOF

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 507 days.

(21) Appl. No.: 12/309,470

(22) PCT Filed: Jul. 20, 2007

(86) PCT No.: PCT/JP2007/064717
§ 371 (c)(1), (2), (4) Date: Jan. 21, 2009

(87) PCT Pub. No.: WO2008/010609
PCT Pub. Date: Jan. 24, 2008

(65) Prior Publication Data
US 2009/0192328 A1    Jul. 30, 2009

(30) Foreign Application Priority Data
Jul. 21, 2006   (JP) ................................. 2006-199127

(51) Int. Cl.
C07C 323/00 (2006.01)
C07C 51/00 (2006.01)
C07C 319/00 (2006.01)

(52) U.S. Cl. ............................ 560/152; 562/538; 568/43

(58) Field of Classification Search .................... None
See application file for complete search history.

(56) References Cited

U.S. PATENT DOCUMENTS

| | | | |
|---|---|---|---|
| 4,524,077 A | 6/1985 | Ruest et al. | |
| 7,504,542 B2 | 3/2009 | Jackstell et al. | |
| 2004/0170669 A1 | 9/2004 | Kunkle et al. | |
| 2005/0215623 A1 | 9/2005 | Giesen et al. | |
| 2007/0265474 A1 | 11/2007 | Hagiya | |
| 2008/0114185 A1 | 5/2008 | Hagiya | |

FOREIGN PATENT DOCUMENTS

| | | |
|---|---|---|
| EP | 0 601 195 | 6/1994 |
| EP | 1 795 602 | 6/2007 |
| EP | 1 801 227 | 6/2007 |
| JP | 2006-136317 | 6/2006 |
| WO | 2004/019683 | 3/2004 |

OTHER PUBLICATIONS

International Search Report dated Nov. 16, 2007 in the International (PCT) Application PCT/JP2007/064717 of which the present application is the U.S. National Stage.

Thomas R. Steadman et al., "A Methionine Substitute: 4-Methylthiobutane-1,2-diol", Journal of Agricultural and Food Chemistry, American Chemical Society, vol. 23, No. 6, pp. 1137-1144, XP002998489, ISSN: 0021-8561, Nov. 1975.

Examination Report issued Jan. 21, 2010 in Singapore Patent Application No. 2008095440 corresponding to the present U.S. application.

Matsumoto, T. et al., *Selective Formation of Triose from Formaldehyde Catalyzed by Thiazolium Salt*, Journal of American Chemical Society, vol. 106, No. 17 (1984), pp. 4829-4832.

Kim, H. P. et al., *Synthesis of New Antiinflammatory Steroidal 20-Carboxamides: (20R)- and (20S)-21-(N-Substituted amino)-11β,17,20-trihydroxy-3,21-dioxo-1,4-pregnadiene, Journal of Medicinal Chemistry*, vol. 30, No. 12 (1987), pp. 2239-2244.

Teles, J. H. et al., *The Chemistry of Stable Carbenes*, Helvetica Chimica Acta, vol. 79 (1996), pp. 61-83.

Pohl, M. et al., *Thiamin-Diphosphate-Dependent Enzymes: New Aspect of Asymmetric C-C Bond Formation*, Chemical European Journal, vol. 8, No. 23 (2002), pp. 5288-5295.

PCT Written Opinion (in English) dated Jan. 27, 2009 in the International (PCT) Application PCT/JP2007/064717 of which the present application is the U.S. National Stage.

*Primary Examiner* — Paul A Zucker

(74) *Attorney, Agent, or Firm* — Wenderoth, Lind & Ponack L.L.P.

(57) ABSTRACT

A process for producing a 2-hydroxy-4-(methylthio)butyrate compound represented by the formula (2):

$$CH_3S\text{-}CH_2CH_2\text{-}CH(OH)\text{-}C(=O)\text{-}O\text{-}A \quad (2)$$

wherein A is a hydrogen atom or a group represented by $R\text{—}CH_2\text{—}$, wherein R is a hydrogen atom or an alkyl group, which comprises the step of:
reacting 4-(methylthio)-2-oxo-1-butanol with oxygen and a compound represented by the formula (1):

$$A\text{-}OH \quad (1)$$

wherein A is as defined above, in the presence of a copper compound.

16 Claims, No Drawings

PROCESS FOR PRODUCING 2-HYDROXY-4-(METHLTHIO)BUTYRATE COMPOUNDS AND INTERMEDIATES THEREOF

TECHNICAL FIELD

The present invention related to a process for producing 2-hydroxy-4-(methylthio)butyrate compounds and intermediates thereof.

BACKGROUND ART

A 2-hydroxy-4-(methylthio)butyrate compound represented by the formula (2):

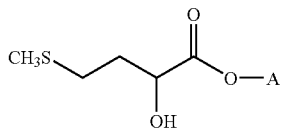

(2)

wherein A is a hydrogen atom or a group represented by R—CH$_2$—, wherein R is a hydrogen atom or an alkyl group, is known as a starting material for synthesizing analogs of L-methionine, the essential amino acid, or penem antibiotics (see U.S. Pat. No. 4,524,077 and EP 338735 A). As a process for producing a typical compound thereof, 2-hydroxy-4-(methylthio)butyric acid, JP 5-1787 B discloses the reaction of 3-(methylthio)propionaldehyde and hydrogen cyanide to obtain 2-hydroxy-4-(methylthio)butyronitrile, followed hydrolysis of the 2-hydroxy-4-(methylthio)butyronitrile thus obtained with a strong acid such as sulfuric acid. Also, JP 2006-136317A discloses a process using 1,2-epoxy-3-butene as a staring material.

DISCLOSURE OF THE INVENTION

The present invention provides:

1. A process for producing a 2-hydroxy-4-(methylthio) butyrate compound represented by the formula (2):

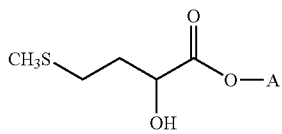

(2)

wherein A is a hydrogen atom or a group represented by R—CH$_2$—, wherein R is a hydrogen atom or an alkyl group, which comprises the step of:

reacting 4-(methylthio)-2-oxo-1-butanol with oxygen and a compound represented by the formula (1):

A-OH (1)

wherein A is as defined above, in the presence of a copper compound;

2. The process for producing a 2-hydroxy-4-(methylthio) butyrate compound according to the above item 1, wherein A is a hydrogen atom, and the reaction is performed in the presence of a base;

3. The process for producing a 2-hydroxy-4-(methylthio) butyrate compound according to the above item 1 or 2, wherein the copper compound is a bivalent copper compound;

4. The process for producing a 2-hydroxy-4-(methylthio) butyrate compound according to the above item 3, wherein the bivalent copper compound is copper acetate (II), copper (II) acetylacetonate, copper carbonate (II), copper chloride (II), copper sulfate (II), copper hydroxide (II) or copper oxide (II);

5. The process for producing a 2-hydroxy-4-(methylthio) butyrate compound according to the above item 2, wherein the base is an alkali metal hydroxide, an alkaline earth metal hydroxide, an alkali metal carbonate, an alkaline earth metal carbonate or an alkali metal bicarbonate;

6. 4-(Methylthio)-2-oxo-1-butanol;

7. A process for producing 4-(methylthio)-2-oxo-1-butanol, which comprises the step of:

reacting formaldehyde with 3-(methylthio)propionaldehyde in the presence of a salt represented by the formula (3):

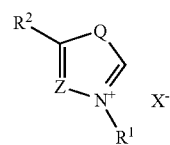

(3)

wherein R$^1$ is an optionally substituted alkyl group or an optionally substituted aryl group;

R$^2$ is an optionally substituted alkyl group, an optionally substituted aryl group, an optionally substituted alkenyl group, a halogen atom or a hydrogen atom;

Q is —S— or —NR$^3$—, and when Q is —S—, then Z is =CR$^4$— and when Q is —NR$^3$—, then Z is =N—, wherein R$^3$ is an alkyl group or an aryl group;

R$^4$ is an optionally substituted alkyl group, an optionally substituted aryl group or an optionally substituted alkenyl group;

R$^2$ and R$^3$ may be combined together with the carbon atom and the nitrogen atom to which they are bonded to form a ring;

R$^2$ and R$^4$ may be combined together with the carbon atoms to which they are bonded to form a ring; and X$^-$ is an anion, and a base;

8. The process for producing 4-(methylthio)-2-oxo-1-butanol according to the above item 7, wherein Q is —S—;

9. The process for producing 4-(methylthio)-2-oxo-1-butanol according to the above item 7 or 8, wherein the base is at least one member selected from the group consisting of a tertiary amine, an alkali metal hydroxide, an alkaline earth metal hydroxide, an alkali metal carbonate, an alkaline earth metal carbonate and an alkali metal bicarbonate;

10. The process for producing 4-(methylthio)-2-oxo-1-butanol according to any one of the above items 7 to 9, wherein the anion is a halide ion, a borate ion, a tetrafluoroborate ion, a phosphate ion, a hexafluorophosphate ion, an antimonate ion, a hexafluoroantimonate ion, a sulfonate ion or an amide ion;

11. A process for producing 4-(methylthio)-2-oxo-1-butanol, which comprises the step of:

reacting formaldehyde with 3-(methylthio)propionaldehyde in the presence of a triazole compound represented by the formula (4):

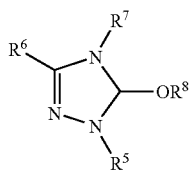

(4)

wherein $R^5$ and $R^6$ are the same or different and each is an optionally substituted alkyl group or an optionally substituted aryl group;

$R^7$ is an optionally substituted alkyl group, an optionally substituted aryl group, an optionally substituted alkenyl group, a halogen atom or a hydrogen atom;

$R^8$ is an optionally substituted alkyl group; and $R^6$ and $R^7$ may be combined together with the carbon atom and the nitrogen atom to which they are bonded to form a ring;

12. The process for producing 4-(methylthio)-2-oxo-1-butanol according to the above item 11, wherein the triazole compound represented by the formula (4) is 5-methoxy-1,3,4-triphenyl-4,5-dihydro-1H-1,2,4-triazole or 5-ethoxy-1,3,4-triphenyl-4,5-dihydro-1H-1,2,4-triazole;

13. 4-(Methylthio)-2-oxo-1-butanal;

14. A process for producing a 2-hydroxy-4-(methylthio)butyrate compound represented by the formula (2):

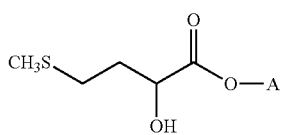

(2)

wherein A is as defined above, which comprises the steps of:

reacting formaldehyde with 3-(methylthio)propionaldehyde in the presence and a salt represented by the formula (3):

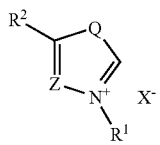

(3)

wherein $R^1$ is an optionally substituted alkyl group or an optionally substituted aryl group;

$R^2$ is an optionally substituted alkyl group, an optionally substituted aryl group, an optionally substituted alkenyl group, a halogen atom or a hydrogen atom;

Q is —S— or —$NR^3$—, and when Q is —S—, then Z is =$CR^4$— and when Q is —$NR^3$—, then Z is =N—, wherein $R^3$ is an alkyl group or an aryl group;

$R^4$ is an optionally substituted alkyl group, an optionally substituted aryl group or an optionally substituted alkenyl group;

$R^2$ and $R^3$ may be combined together with the carbon atom and the nitrogen atom to which they are bonded to form a ring;

$R^2$ and $R^4$ may be combined together with the carbon atoms to which they are bonded to form a ring; and $X^-$ is an anion, and a base to obtain 4-(methylthio)-2-oxo-1-butanol, and reacting the 4-(methylthio)-2-oxo-1-butanol thus obtained with oxygen and a compound represented by the formula (1):

A-OH (1)

wherein A represents a hydrogen atom or a group represented by R—$CH_2$—, wherein R is a hydrogen atom or an alkyl group; in the presence of a copper compound to obtain the 2-hydroxy-4-(methylthio)butyrate compound; and 15. A process for producing a 2-hydroxy-4-(methylthio)butyrate compound represented by the formula (2):

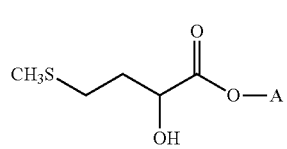

(2)

wherein A is as defined above, which comprises the steps of:

reacting formaldehyde with 3-(methylthio)propionaldehyde in the presence of a triazole compound represented by the formula (4):

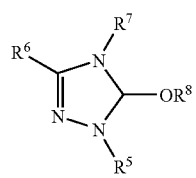

(4)

wherein $R^5$ and $R^6$ are the same or different and each is an optionally substituted alkyl group or an optionally substituted aryl group;

$R^7$ is an optionally substituted alkyl group, an optionally substituted aryl group, an optionally substituted alkenyl group, a halogen atom or a hydrogen atom;

$R^8$ is an optionally substituted alkyl group; and $R^6$ and $R^7$ may be combined together with the carbon atom and the nitrogen atom to which they are bonded to form a ring, to obtain 4-(methylthio)-2-oxo-1-butanol, and reacting the 4-(methylthio)-2-oxo-1-butanol with oxygen and a compound represented by the formula (1):

A-OH (1)

wherein A is a hydrogen atom or a group represented by R—$CH_2$—, wherein R is a hydrogen atom or an alkyl group, in the presence of a copper compound to obtain the 2-hydroxy-4-(methylthio)butyrate compound.

BEST MODE FOR PERFORMING THE INVENTION

First, a process for producing a 2-hydroxy-4-(methylthio) butyrate compound represented by the formula (2):

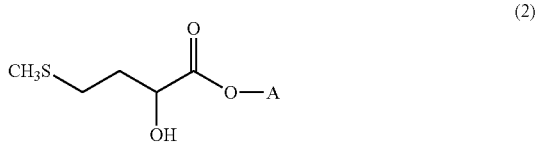

(2)

wherein A is a hydrogen atom or a group represented by R—CH$_2$—, wherein R is a hydrogen atom or an alkyl group (hereinafter abbreviated to the butyrate compound (2)), comprising the step of: reacting 4-(methylthio)-2-oxo-1-butanol with oxygen and a compound represented by the formula (1):

A-OH (1)

wherein A is as defined above (hereinafter abbreviated to the compound (1)), in the presence of a copper compound, will be illustrated.

Either monovalent copper compounds or bivalent copper compounds can be used as the copper compound. Preferably the bivalent copper compounds are used. The copper compounds may be hydrates or anhydrides.

Examples of the monovalent copper compound include copper chloride (I), copper oxide (I), and the like; and examples of the bivalent copper compound include copper acetate (II), copper (II) acetylacetonate, copper carbonate (II), copper chloride (II), copper sulfate(II), copper hydroxide (II), copper oxide (II), and the like.

The amount of the copper compound used is usually 0.001 mole or more per 1 mole of 4-(methylthio)-2-oxo-1-butanol. The upper limit thereof is not particularly limited, but is practically 0.2 mole or less per 1 mole of 4-(methylthio)-2-oxo-1-butanol, considering the economic aspects.

Oxygen gas can be used alone, and oxygen gas diluted with an inert gas such as nitrogen gas can also be used. In addition, air can be used.

The amount of the oxygen used is usually 1 mole or more per 1 mole of 4-(methylthio)-2-oxo-1-butanol, and the upper limit thereof is not particularly limited.

In the compound (1), A is a hydrogen atom or a group: R—CH$_2$—, and R is a hydrogen atom or an alkyl group. Examples of the alkyl group include linear or branched alkyl groups having 1 to 6 carbon atoms such as a methyl group, an ethyl group, a n-propyl group, an isopropyl group, a n-butyl group, an isobutyl group, a sec-butyl group, a tert-butyl group, a n-pentyl group, a n-hexyl group, and the like.

Examples of the compound (1) include water, methanol, ethanol, 1-propanol, 1-butanol, 1-pentanol, 1-hexanol, and the like.

The amount of the compound (1) used is usually 1 mole or more per 1 mole of 4-(methylthio)-2-oxo-1-butanol, and the upper limit thereof is not particularly limited. A large excess amount may be used so that the compound also serves as a solvent.

When water is used as the compound (1), it is preferable to perform the reaction in the presence of a base. Examples of the base include alkali metal hydroxides such as sodium hydroxide, potassium hydroxide, lithium hydroxide, etc.; alkaline earth metal hydroxides such as magnesium hydroxide, calcium hydroxide, etc.; alkali metal carbonates such as sodium carbonate, potassium carbonate, lithium carbonate, etc.; alkaline earth metal carbonates such as magnesium carbonate, calcium carbonate, etc.; alkali metal bicarbonates such as sodium bicarbonate, potassium bicarbonate, lithium bicarbonate, etc.; and the like.

The amount of the base used is usually from 0.1 to 10 moles per 1 mole of the copper compound.

The reaction of 4-(methylthio)-2-oxo-1-butanol with oxygen and the compound (1) is usually performed in a solvent. Examples of the solvent include ether solvents such as diethyl ether, methyl tert-butyl ether, tetrahydrofuran, etc.; ester solvents such as ethyl acetate, etc.; tertiary alcohol solvents such as tert-butanol, etc.; nitrile solvents such as acetonitrile, propionitrile, etc.; and the like. As mentioned above, the compound (1) itself can be used as the solvent. It is preferable to use the compound (1) as the solvent. The amount of the solvent used is not particularly limited, but it is practical that the amount thereof is 100 times by weight or less relative to that of 4-(methylthio)-2-oxo-1-butanol, considering the volume efficiency, and the like.

When the reaction temperature is too low, the reaction hardly proceeds. On the other hand, when the temperature is too high, side reactions tends to be promoted. In view of these reasons, the temperature is usually from −10 to 120° C., preferably from 0 to 80° C.

The reaction is usually performed at normal pressure, but may be performed under pressure or reduced pressure.

The reaction is performed in such a manner that the copper compound, 4-(methylthio)-2-oxo-1-butanol, oxygen, the compound (1) and, if necessary, the base are brought into contact. The order is not particularly limited. Usually, 4-(methylthio)-2-oxo-1-butanol, the compound (1), the copper compound and, if necessary, the base are mixed, and the resulting mixture is stirred under an oxygen atmosphere; or oxygen is bubbled into the above-mentioned mixture.

The progress of the reaction can be confirmed by using, for example, a conventional analytical means such as gas chromatography, high performance liquid chromatography, thin layer chromatography, nuclear magnetic resonance spectroscopic analysis, infrared absorption spectroscopic analysis, etc.

Although the mechanism of this reaction is not elucidated, it can be presumed that 4-(methylthio)-2-oxo-1-butanal would be formed as an intermediate and the reaction proceeds via 4-(methylthio)-2-oxo-1-butanal.

After completion of the reaction, for example, the reaction mixture is mixed with an acid to neutralize or acidify the reaction mixture, and, if necessary, water or a water-insoluble solvent is added to the reaction mixture to extract a product, thereby obtaining an organic layer including the butyrate compound (2). The extract is concentrated to isolate the resulting butyrate compound (2). The isolated butyrate compound (2) can be further purified by using a conventional purification technique such as distillation, column chromatography, recrystallization, and the like. As the acid, usually, sulfuric acid, hydrochloric acid, etc. can be used.

Examples of the water-insoluble organic solvent include ester solvents such as ethyl acetate, etc.; ether solvents such as methyl tert-butyl ether, etc.; hydrocarbon solvents such as hexane; heptane, toluene, xylene, etc.; and the like. The amount thereof is not particularly limited.

Examples of the butyrate compound (2) thus obtained include 2-hydroxy-4-(methylthio)butyric acid, methyl 2-hydroxy-4-(methylthio)butyrate, ethyl 2-hydroxy-4-(methylthio)butyrate, n-propyl 2-hydroxy-4-(methylthio)butyrate, n-butyl 2-hydroxy-4-(methylthio)butyrate, and the like.

The starting material, 4-(methylthio)-2-oxo-1-butanol is a novel compound, and it can be produced by reacting formaldehyde with 3-(methylthio)propionaldehyde in the presence of a base and a salt represented by the formula (3):

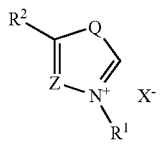
(3)

wherein $R^1$ is an optionally substituted alkyl group or an optionally substituted aryl group;

$R^2$ an optionally substituted alkyl group, an optionally substituted aryl group, an optionally substituted alkenyl group, a halogen atom or a hydrogen atom;

Q is —S— or —$NR^3$—, and when Q is —S—, then Z is =$CR^4$— and when Q is —$NR^3$—, then Z is =N—, wherein $R^3$ is an alkyl group or an aryl group;

$R^4$ is an optionally substituted alkyl group, an optionally substituted aryl group or an optionally substituted alkenyl group;

$R^2$ and $R^3$ may be combined together with the carbon atom and the nitrogen atom to which they are bonded to form a ring;

$R^2$ and $R^4$ may be combined together with the carbon atoms to which they are bonded to form a ring; and $X^-$ is an anion (hereinafter, abbreviated to the salt (3)).

As 3-(methylthio)propionaldehyde, either a commercial available one can be used, or it can be produced according to a known process such as the reaction of acrolein with methanethiol in the presence of acetic acid and pyridine (see U.S. Pat. No. 5,250,743), or the like.

As formaldehyde, usually, a commercially available one can be used as it is, or it can be used in the form of an aqueous solution. In addition, formaldehyde polymers capable of producing formaldehyde by decomposition or depolymerization under reaction conditions, such as trioxane, paraformaldehyde, etc. can also be used as formaldehyde. As such a formaldehyde polymer, usually, a commercially available product can be used. Among them, trioxane and paraformaldehyde are preferable, and paraformaldehyde is more preferable.

When formaldehyde is used, the amount thereof to be used is usually 1 mole or more per 1 mole of 3-(methylthio)propionaldehyde. The upper limit thereof is not particularly limited, but it is practically 10 moles or less per 1 mole of 3-(methylthio)propionaldehyde, considering the economic aspects. When a formaldehyde polymer is used, the amount thereof to be used can be decided so that the amount of formaldehyde derived from the polymer becomes 1 mole or more per 1 mole of 3-(methylthio)propionaldehyde. For example, when trioxane is used as the formaldehyde polymer, trioxane is used in an amount of 1 mole or more per 3 moles of 3-(methylthio)propionaldehyde because 1 mole of the trioxane corresponds to 3 moles of formaldehyde.

In the formula (3), examples of the optionally substituted alkyl group include linear, branched, or cyclic unsubstituted alkyl groups having 1 to 20 carbon atoms such as a methyl group, an ethyl group, a n-propyl group, an isopropyl group, a n-butyl group, an isobutyl group, a sec-butyl group, a tert-butyl group, a n-pentyl group, an n-decyl group, a cyclopropyl group, a 2,2-dimethylcyclopropyl group, a cyclopentyl group, a cyclohexyl group, a menthyl group, etc.; and such alkyl groups whose at least one hydrogen atom is substituted with a substituent, e.g., an alkoxy group having 1 to 20 carbon atoms such as a methoxy group, an ethoxy group, etc.; a halogen atom such as a fluorine atom, etc.; an acyl group having 1 to 10 carbon atoms such as a formyl group, an acetyl group, a propionyl group, a benzoyl group, etc.; an alkoxycarbonyl group having 2 to 10 carbon atoms such as a methoxycarbonyl group, an ethoxycarbonyl group, etc.; an aryl group having 6 to 20 carbon atoms such as a phenyl group, a 1-naphthyl group, 2-naphthyl group, 4-methylphenyl group, etc.; an alkenyl group having 2 to 20 carbon atoms such as an ethenyl group, a 2-propenyl group, etc.; an alkynyl group having 2 to 20 carbon atoms such as a 2-propynyl group, etc.; a carboxyl group; an amino group; a hydroxyl group, and the like. Specific examples of the substituted alkyl group include a fluoromethyl group, a trifluoromethyl group, a methoxymethyl group, an ethoxymethyl group, a 3-oxobutyl group, a methoxyethyl group, a methoxycarbonylmethyl group, a benzyl group, a 2-propenyl group, a 2-propynyl group, an aminomethyl group, a 1-carboxybutyl group, a 2-hydroxymethyl group, and the like.

Examples of the optionally substituted aryl group include unsubstituted aryl groups having 6 to 20 carbon atoms such as a phenyl group, a 1-naphthyl group, a 2-naphthyl group, a 4-methylphenyl group, 4-phenylphenyl group, etc.; and such aryl groups whose at least one hydrogen atom is substituted with a substituent, e.g., the above-mentioned halogen atom; the above-mentioned alkoxy group having 1 to 20 carbon atoms; the above-mentioned acyl group having 2 to 10 carbon atoms; the above-mentioned alkoxycarbonyl group having 2 to 10 carbon atoms; a cyano group; a nitro group; and the like. Specific examples of the substituted aryl group include a 4-chlorophenyl group, a 4-methoxyphenyl group, a 4-acetylphenyl group, and the like.

Examples of the optionally substituted alkenyl group include unsubstituted linear, branched or cyclic alkenyl groups having 2 to 12 carbon atoms such as an ethenyl group, a 1-propenyl group, a 1-methylethenyl group, a 1-butenyl group, a 1-methyl-1-propenyl group, a 2-methyl-1-propenyl group, a 1-pentenyl group, a 1-hexenyl group, a 1-decenyl group, a 1-cyclopentenyl group, a 1-cyclohexenyl group, etc.; and such alkenyl groups whose at least one hydrogen atom is substituted with a substituent, e.g., the above-mentioned halogen atom; the above-mentioned alkoxy group having 1 to 20 carbon atoms; the above-mentioned aryl group having 6 to 20 carbon atoms; an aryloxy group having 6 to 20 carbon atoms such as a phenoxy group, a 1-naphthoxy group, a 2-naphthoxy group, etc.; the above-mentioned acyl group having 2 to 10 carbon atoms; and the like. Specific examples of the substituted alkenyl group include a 3-fluoro-1-propenyl group, a 3-methoxy-1-propenyl group, a 3-phenoxy-1-butenyl group, a styryl group, and the like.

Examples of the halogen atom represented by $R^2$ include a fluorine atom, a chlorine atom, a bromine atom, an iodine atom, and the like.

Examples of the alkyl group represented by $R^3$ include alkyl groups having 1 to 6 carbon atoms such as a methyl group, an ethyl group, an n-propyl group, etc., and examples of the aryl groups include aryl groups having 6 to 10 carbon atoms such as a phenyl group, a naphthyl group, etc.

The ring formed by combining $R^2$ and $R^3$ together with the carbon atom and the nitrogen atom to which they are bonded include a pyridine ring, and the like; and the ring formed by combining $R^2$ and $R^4$ together with the carbon atoms to which they are bonded include a cyclopentene ring, a cyclohexene ring, a cycloheptene ring, a benzene-ring, and the like.

Examples of the anion include halide ions such as a fluoride ion, a chloride ion, a bromine ion, an iodide ion; a borate ion; a tetrafluoroborate ion; a phosphate ion; a hexafluorophosphate ion; an antimonate ion; a hexafluoroantimonate ion; sulfonate ions such as a methanesulfonate ion, a p-toluenesulfonate ion, a trifluoromethanesulfonate ion, etc.; amide ions such as a bis(trifluoromethylsulfonyl)amide ion, etc.; and the like.

As such the salt (3), usually, a commercially available one can be used.

Examples of the salt (3) include 3-methylthiazolium bromide, 3-ethylthiazolium bromide, 3-n-propylthiazolium bromide, 3-n-butylthiazolium bromide, 3,5-dimethylthiazolium chloride, 3-ethyl-5-(2-hydroxymethyl)-4-methylthiazolium bromide, 3-benzylthiazolium bromide, 3-benzylthiazolium chloride, 3-benzyl-4-methylthiazolium bromide, 3-benzyl-4-methylthiazolium chloride, 3-benzyl-5-methylthiazolium bromide, 3-benzyl-5-methylthiazolium chloride, 3-ethylbenzothiazolium bromide, 3-ethylbenzothiazolium chloride, 3-benzylbenzothiazolium bromide, 3-benzylbenzothiazolium chloride, 3-(2-propene-1-yl)benzothiazolium bromide, 3-benzylthiazolium trifluoromethanesulfonate, 3-benzylthiazolium hexafluorophosphate, 3-benzylthiazolium hexafluoroantimonate, 3-benzylthiazolium bis(trifluoromethanesulfonyl)amide, 1,3,4-tri(4-chlorophenyl)-4H-1,2,4-triazolium tetrafluoroborate, 1,3,4-tri(4-methoxyphenyl)-4H-1,2,4-triazolium tetrafluoroborate, 2-phenyl-1,2,4-triazolo[4,3-a]pyridinium tetrafluoroborate, and the like.

Examples of the base include tertiary amines, alkali metal hydroxides, alkaline earth metal hydroxides, alkali metal carbonates, alkali metal carbonates, alkali metal bicarbonates, and the like.

Examples of the tertiary amine include trimethylamine, triethylamine, diisopropylethylamine, tributyl amine, and the like. Examples of the alkali metal hydroxide include sodium hydroxide, potassium hydroxide, lithium hydroxide, and the like. Examples of the alkaline earth metal hydroxide include magnesium hydroxide, calcium hydroxide, and the like. Examples of the alkali metal carbonate include sodium carbonate, potassium carbonate, lithium carbonate, and the like. Examples of the alkaline earth metal carbonate include magnesium carbonate, calcium carbonate, and the like. Examples of the alkali metal bicarbonate include sodium bicarbonate, potassium bicarbonate, lithium bicarbonate, and the like.

The amount of the salt (3) used is usually 0.001 mole or more per 1 mole of 3-(methylthio)propionaldehyde. The upper limit thereof is not particularly limited, but it is practically 0.2 mole or less, considering the economic aspects. The amount of the base used is usually from 0.1 to 1 mole, preferably from 0.5 to 1 mole, per 1 mole of the salt (3).

Further, 4-(methylthio)-2-oxo-1-butanol can also be produced by reacting formaldehyde with 3-(methylthio)propionaldehyde in the presence of a triazole compound represented by the formula (4):

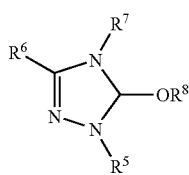

(4)

wherein $R^5$ and $R^6$ are the same or different and each is an optionally substituted alkyl group or an optionally substituted aryl group;

$R^7$ is an optionally substituted alkyl group, an optionally substituted aryl group, an optionally substituted alkenyl group, a halogen atom or a hydrogen atom;

$R^8$ is an optionally substituted alkyl group; and $R^6$ and $R^7$ may be combined together with the carbon atom and the nitrogen atom to which they are bonded to form a ring (hereinafter, abbreviated to the triazole compound (4)).

In the formula (4), as the optionally substituted alkyl groups, the optionally substituted aryl groups, the optionally substituted alkenyl groups, and the halogen atom, the same groups and atoms as listed above may be used.

Examples of the triazole compound (4) include 5-methoxy-1,3,4-triphenyl-4,5-dihydro-1H-1,2,4-triazole, 5-ethoxy-1,3,4-triphenyl-4,5-dihydro-1H-1,2,4-triazole, 5-propoxy-1,3,4-triphenyl-4,5-dihydro-1H-1,2,4-triazole, 5-methoxy-4-methyl-1,3-diphenyl-4,5-dihydro-1H-1,2,4-triazole, 5-ethoxy-4-methyl-1,3-diphenyl-4,5-dihydro-1H-1,2,4-triazole, 5-methoxy-4-(4-chlorophenyl)-1,3-diphenyl-4,5-dihydro-1H-1,2,4-triazole, 2,3-dihydro-3-methoxy-2-phenyl-1,2,4-triazolo[4,3-a]pyridine, and the like; and 5-methoxy-1,3,4-triphenyl-4,5-dihydro-1H-1,2,4-triazole and 5-ethoxy-1,3,4-triphenyl-4,5-dihydro-1H-1,2,4-triazole are preferable. As the triazole compound (4), a commercially available one can be used. Alternatively, for example, the triazole compound (4) to be used can be produced by reacting a salt represented by the formula (5):

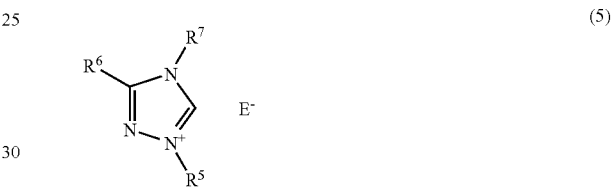

(5)

wherein $R^5$, $R^6$ and $R^7$ are as defined above, and $E^-$ is a monovalent anion, with an alkali metal alkoxide represented by the formula (6):

$$M^+ {}^-OR^8 \quad (6)$$

wherein $R^8$ is as defined above, and M is an alkali metal atom.

As the monovalent anion in the formula (5), the same anions as those in the above-mentioned $X^-$ can be exemplified. Examples of the alkali metal atom in the formula (6) include a sodium atom, a potassium atom, and the like. As the salt represented by the formula (5) and the alkali metal alkoxide represented by the formula (6), usually, commercially available products can be used.

The amount of the triazole compound (4) used is usually 0.001 mole or more per 1 mole of 3-(methylthio)propionaldehyde. The upper limit thereof is not particularly limited, but it is practically 0.2 mole or less per 1 mole of 3-(methylthio)propionaldehyde, considering the economic aspects.

When the triazole compound (4) is used, the amount of formaldehyde used is the same manner as that in case of using the salt (3).

Usually, 3-(methylthio)propionaldehyde is reacted with formaldehyde in the presence of a solvent. The solvents are not particularly limited as long as they are inert solvents. Examples thereof include water; ether solvents such as diethyl ether, methyl tert-butyl ether, tetrahydrofuran, ethylene glycol dimethyl ether, etc.; ester solvents such as ethyl acetate, etc.; secondary or tertiary alcohol solvents such as isopropanol, tert-butanol, etc.; nitrile solvents such as acetonitrile, propionitrile, etc.; aromatic hydrocarbon solvents such as toluene, xylene, etc.; and the like. They can be used alone or as a mixture thereof. The amount of the solvent used is not particularly limited, but it is practically 100 times by weight or less relative to that of the 3-(methylthio)propionaldehyde, considering the volume efficiency, and the like.

When the reaction temperature is too low, the reaction hardly proceeds. On the other hand, when the temperature is too high, side reactions tends to be promoted. In view of these reasons, the temperature is usually from −10 to 200° C., preferably from 20 to 120° C.

The reaction is usually performed at normal pressure, but may be performed under pressure or reduced pressure.

When 3-(methylthio)propionaldehyde is reacted with formaldehyde using the salt (3) and the base, the reaction is performed by contacting and mixing 3-(methylthio)propionaldehyde, formaldehyde, the salt (3) and the base. The order of the mixing is not particularly limited, but it is preferable that 3-(methylthio)propionaldehyde is mixed with formaldehyde and the salt (3), and then the base is added to the resulting mixture to perform the reaction. When 3-(methylthio)propionaldehyde is reacted with formaldehyde using the triazole compound (4), the reaction is preformed by contacting and mixing 3-(methylthio)propionaldehyde, formaldehyde and the triazole compound (4), and the mixing order is not particularly limited.

The progress of the reaction can be confirmed by using, for example, a conventional analytical means such as gas chromatography, high performance liquid chromatography, thin layer chromatography, nuclear magnetic resonance spectroscopic analysis, infrared absorption spectroscopic analysis, and the like.

After completion of the reaction, if necessary, water or a water-insoluble organic solvent is added to the reaction mixture to extract a product, and the resulting organic layer can be concentrated to isolate 4-(methylthio)-2-oxo-1-butanol. Examples of the water-insoluble organic solvent include ester solvents such as ethyl acetate, etc.; ether solvents such as tert-butyl methyl ether, etc.; hydrocarbon solvents such as hexane, heptane, toluene, xylene, etc.; and the like. The amount thereof is not particularly limited. The isolated 4-(methylthio)-2-oxo-1-butanol can be further purified by a conventional purification technique such as distillation, column chromatography, recrystallization, and the like.

EXAMPLES

The present invention will be illustrated in detail by means of Examples, but the present invention is not limited thereto. The analysis was performed by a gas chromatography area percentage method.

Example 1

A 200 mL flask equipped with a magnet rotor was charged with 3-(methylthio)propionaldehyde (23.7 g), paraformaldehyde (17.7 g), 3-ethylbenzothiazolium bromide (4 g) and tert-butanol (100 g) at room temperature. Further, triethylamine (1.3 g) was added to the resulting solution, and the mixture was maintained with stirring at an inner temperature of 80° C. for 24 hours. After completion of the reaction, ethyl acetate (100 g) was added to the reaction mixture, and the resulting mixture was washed with water (20 g) twice to obtain a solution containing 4-(methylthio)-2-oxo-1-butanol. The solution was concentrated to obtain an oily concentrated residue. The concentrated residue was distilled under reduced pressure conditions to obtain a fraction containing 4-(methylthio)-2-oxo-1-butanol (15 g; distillation temperature: 85 to 95° C.; operation pressure: 0.3 kPa). The fraction thus obtained contained 40% of 4-(methylthio)-2-oxo-1-butanol. The fraction was purified by using a silica gel column (solvent; ethyl acetate:n-hexane=1:4, followed by ethyl acetate: n-hexane=2:4) to obtain a solution containing 4-(methylthio)-2-oxo-1-butanol. The solution thus obtained was distilled to obtain a fraction containing 4-(methylthio)-2-oxo-1-butanol (1.4 g; content: 91%) and a fraction containing 4-(methylthio)-2-oxo-1-butanol (2.0 g; content: 82%). Both of the fractions solidified at room temperature.

$^1$H-NMR (δ/ppm, dimethyl sulfoxide-$d_6$, tetramethylsilane standard) 2.05 (s, 3H), 2.62 (m, 2H), 2.70 (m, 2H), 4.06 (s, 2H), 5.13 (bs, 1H)

MS: m/z 134 (M$^+$), 106, 103, 86, 75, 61

Example 2

A 200 mL flask equipped with a magnet rotor was charged with 3-(methylthio)propionaldehyde (25.0 g), paraformaldehyde (20.0 g), 3-benzylthiazolium bromide (3 g) and ethyleneglycol dimethyl ether (100 g) at room temperature. Further, potassium carbonate (800 mg) was added to the resulting solution, and the mixture was maintained with stirring at an inner temperature of 50° C. for 6 hours. After completion of the reaction, the reaction was concentrated to remove ethyleneglycol dimethyl ether. The resulting concentrated residue was mixed with toluene (50 g) and water (50 g). After stirring the resulting mixture, the mixture was allowed to stand to separate into an organic layer and an aqueous layer. The aqueous layer was extracted with toluene (50 g), and the toluene layer thus obtained was mixed with the organic layer. The resulting organic layer was concentrated to obtain oil containing 4-(methylthio)-2-oxo-1-butanol. The oil was distilled under reduced pressure to obtain a fraction containing 4-(methylthio)-2-oxo-1-butanol (7.0 g; distillation temperature: 110 to 115° C.; operation pressure: 0.7 kPa). The content was 86%.

Example 3

A 50 mL flask equipped with a magnet rotor was charged with 3-(methylthio)propionaldehyde (300 mg), paraformaldehyde (300 mg), 3-ethylbenzothiazolium bromide (60 mg) and tert-butanol (3 g) at room temperature. Further, triethylamine (40 mg) was added to the resulting solution, and the mixture was maintained with stirring at an inner temperature of 80° C. for 24 hours. After completion of the reaction, ethyl acetate (10 g) was added to the reaction mixture, followed by washing with water (5 g) twice. The solution thus obtained was concentrated to obtain pale yellow oil containing 4-(methylthio)-2-oxo-1-butanol (400 mg). The content was 40%, the yield was 41%, and 45% of 3-(methylthio)propylaldehyde remained.

Example 4

A 50 mL flask equipped with a magnet rotor was charged with 3-(methylthio)propionaldehyde (500 mg), paraformaldehyde (400 mg), 3-benzylthiazolium bromide (61 mg) and tert-butanol (3 g) at room temperature. After addition of potassium carbonate (16 mg) to the resulting solution, the mixture was maintained with stirring at an inner temperature of 50° C. for 6 hour. After completion of the reaction, ethyl acetate (10 g) was added to the reaction mixture, followed by washing with water (5 g) twice. The solution thus obtained was concentrated to obtain pale yellow oil (680 mg) containing 4-(methylthio)-2-oxo-1-butanol. The content was 49%, the yield was 52%, and 32% of 3-(methylthio)propylaldehyde remained.

Example 5

A 50 mL flask equipped with a magnet rotor was charged with 3-(methylthio)propionaldehyde (500 mg), paraformaldehyde (400 mg), 3-benzylthiazolium bromide (61 mg) and tert-butanol (3 g) at room temperature. After addition of potassium hydroxide (14 mg) to the resulting solution, the mixture was maintained with stirring at 80° C. for 6 hours. After completion of the reaction, ethyl acetate (10 g) was added to the reaction mixture, followed by washing with water (5 g) twice. The solution thus obtained was concentrated to obtain pale yellow oil (670 mg) containing 4-(methylthio)-2-oxo-1-butanol. The content was 32%, the yield was 34%, and 28% of 3-(methylthio)propylaldehyde remained.

Example 6

A 50 mL flask equipped with a magnet rotor was charged with 3-(methylthio)propionaldehyde (500 mg), paraformaldehyde (400 mg), 3-benzylthiazolium bromide (61 mg) and toluene (3 g) at room temperature. After addition of potassium carbonate (16 mg) to the mixture, the resulting mixture was maintained with stirring at an inner temperature of 110° C. for 2 hours. After completion of the reaction, ethyl acetate (10 g) was added to the reaction mixture, followed by washing with water (5 g) twice. The solution thus obtained was concentrated to obtain pale yellow oil containing 4-(methylthio)-2-oxo-1-butanol (650 mg). The content was 51%, the yield was 52%, and 5% of 3-(methylthio)propylaldehyde remained.

Example 7

A 50 mL flask equipped with a magnet rotor was charged with 3-(methylthio)propionaldehyde (250 mg), paraformaldehyde (200 mg), 5-methoxy-1,3,4-triphenyl-4,5-dihydro-1H-1,2,4-triazole (40 mg) and ethyleneglycol dimethyl ether (2 g) at room temperature. The resulting mixture was maintained with stirring at an inner temperature of 50° C. for 6 hours. After completion of the reaction, ethyl acetate (10 g) was added to the reaction mixture, followed by washing with water (5 g) twice. The solution thus obtained was concentrated to obtain pale yellow oil containing 4-(methylthio)-2-oxo-1-butanol (340 mg). The content was 34%, the yield was 36%, and 58% of 3-(methylthio)propylaldehyde remained.

Example 8

A 50 mL flask equipped with a magnet rotor was charged with 4-(methylthio)-2-oxo-1-butanol (100 mg), copper acetate (II) (10 mg) and water (5 g). After addition of potassium hydroxide (30 mg) to the resulting solution, the mixture was maintained with stirring at room temperature for 2 hours in an atmosphere of air. After completion of the reaction, the reaction mixture was acidified by addition of 5% by weight aqueous solution of sulfuric acid, followed by addition of ethyl acetate (10 g). The resulting mixture was stirred and allowed to stand to separate into an organic layer and an aqueous layer. The organic layer was concentrated to obtain a concentrated residue (130 mg). An $^1$H-NMR analysis using an internal standard showed the concentrated residue thus obtained contained 40% by weight of 2-hydroxy-4-(methylthio)butyric acid. The yield was 46%.

Example 9

A 50 mL flask equipped with a magnet rotor was charged with 4-(methylthio)-2-oxo-1-butanol (100 mg), copper acetate (II) (20 mg) and methanol (5 g). The resulting mixture was maintained with stirring at room temperature for 2 hours in an atmosphere of air. A part of the reaction mixture was sampled, and it was analyzed by using a gas chromatography mass spectrometer to confirm the production of 4-(methylthio)-2-oxo-1-butanal (13%).

MS: m/z 132 (M$^+$), 103, 87, 75, 61

The reaction mixture was maintained with stirring at room temperature for further 3 days in an atmosphere of air. The resulting reaction mixture was acidified by addition of 5% by weight of aqueous solution of sulfuric acid, followed by addition of ethyl acetate (10 g). The resulting mixture was allowed to stand to separate into an organic layer and an aqueous layer. The organic layer was concentrated to obtain a concentrated residue (110 mg). The yield of methyl 2-hydroxy-4-(methylthio)butyrate was 12%, the yield of 4-(methylthio)-2-oxo-1-butanal was 23%, and 34% of 4-(methylthio)-2-oxo-1-butanol remained.

INDUSTRIAL APPLICABILITY

According to the present invention, 2-hydroxy-4-(methylthio)butyrate compound can be produced from 3-(methylthio)propionaldehyde, which is easily obtained, without using any highly poisonous reagent, and accordingly the present invention is industrially useful.

The invention claimed is:

1. A process for producing a 2-hydroxy-4-(methylthio) butyrate compound represented by the formula (2):

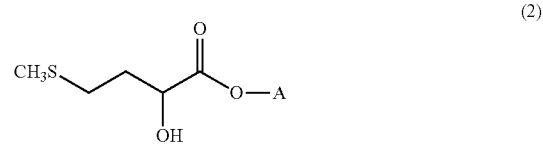

wherein A is a hydrogen atom or a group represented by R—CH$_2$—, wherein R is a hydrogen atom or an alkyl group, which comprises the step of:

reacting 4-(methylthio)-2-oxo-1-butanol with oxygen and a compound represented by the formula (1):

wherein A is as defined above, in the presence of a copper compound.

2. The process for producing a 2-hydroxy-4-(methylthio) butyrate compound according to claim 1, wherein A is a hydrogen atom, and the reaction is performed in the presence of a base.

3. The process for producing a 2-hydroxy-4-(methylthio) butyrate compound according to claim 1, wherein the copper compound is a bivalent copper compound.

4. The process for producing a 2-hydroxy-4-(methylthio) butyrate compound according to claim 3, wherein the bivalent copper compound is copper acetate (II), copper (II) acetylacetonate, copper carbonate (II), copper chloride (II), copper sulfate (II), copper hydroxide (II) or copper oxide (II).

5. The process for producing a 2-hydroxy-4-(methylthio) butyrate compound according to claim 2, wherein the base is an alkali metal hydroxide, an alkaline earth metal hydroxide, an alkali metal carbonate, an alkaline earth metal carbonate or an alkali metal bicarbonate.

6. A process for producing 4-(methylthio)-2-oxo-1-butanol, which comprises the step of:

reacting formaldehyde with 3-(methylthio)propionaldehyde in the presence of a salt represented by the formula (3):

wherein R¹ is an optionally substituted alkyl group or an optionally substituted aryl group;

R² is an optionally substituted alkyl group, an optionally substituted aryl group, an optionally substituted alkenyl group, a halogen atom or a hydrogen atom;

Q is —S— or —NR³—, and when Q is —S—, then Z is =CR⁴— and when Q is —NR³—, then Z is =N—, wherein R³ is an alkyl group or an aryl group;

R⁴ is an optionally substituted alkyl group, an optionally substituted aryl group or an optionally substituted alkenyl group;

R² and R³ may be combined together with the carbon atom and the nitrogen atom to which they are bonded to form a ring;

R² and R⁴ may be combined together with the carbon atoms to which they are bonded to form a ring; and X⁻ is an anion, and a base.

7. The process for producing 4-(methylthio)-2-oxo-1-butanol according to claim 6, wherein Q is —S—.

8. The process for producing 4-(methylthio)-2-oxo-1-butanol according to claim 6, wherein the base is at least one member selected from the group consisting of a tertiary amine, an alkali metal hydroxide, an alkaline earth metal hydroxide, an alkali metal carbonate, an alkaline earth metal carbonate and an alkali metal bicarbonate.

9. The process for producing 4-(methylthio)-2-oxo-1-butanol according to claim 6, wherein the anion is a halide ion, a borate ion, a tetrafluoroborate ion, a phosphate ion, a hexafluorophosphate ion, an antimonate ion, a hexafluoroantimonate ion, a sulfonate ion or an amide ion.

10. A process for producing 4-(methylthio)-2-oxo-1-butanol, which comprises the step of:

reacting formaldehyde with 3-(methylthio)propionaldehyde in the presence of a triazole compound represented by the formula (4):

wherein R⁵ and R⁶ are the same or different and each is an optionally substituted alkyl group or an optionally substituted aryl group;

R⁷ is an optionally substituted alkyl group, an optionally substituted aryl group, an optionally substituted alkenyl group, a halogen atom or a hydrogen atom;

R⁸ is an optionally substituted alkyl group; and

R⁶ and R⁷ may be combined together with the carbon atom and the nitrogen atom to which they are bonded to form a ring.

11. The process for producing 4-(methylthio)-2-oxo-1-butanol according to claim 10, wherein the triazole compound represented by the formula (4) is 5-methoxy-1,3,4-triphenyl-4,5-dihydro-1H-1,2,4-triazole or 5-ethoxy-1,3,4-triphenyl-4,5-dihydro-1H-1,2,4-triazole.

12. A process for producing a 2-hydroxy-4-(methylthio) butyrate compound represented by the formula (2):

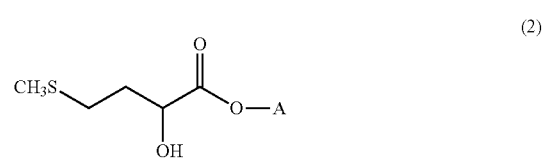

wherein A is as defined above, which comprises the steps of:

reacting formaldehyde with 3-(methylthio)propionaldehyde in the presence and a salt represented by the formula (3):

wherein R¹ is an optionally substituted alkyl group or an optionally substituted aryl group;

R² is an optionally substituted alkyl group, an optionally substituted aryl group, an optionally substituted alkenyl group, a halogen atom or a hydrogen atom;

Q is —S— or —NR³—, and when Q is —S—, then Z is =CR⁴— and when Q is —NR³—, then Z is =N—, wherein R³ is an alkyl group or an aryl group;

R⁴ is an optionally substituted alkyl group, an optionally substituted aryl group or an optionally substituted alkenyl group;

R² and R³ may be combined together with the carbon atom and the nitrogen atom to which they are bonded to form a ring;

R² and R⁴ may be combined together with the carbon atoms to which they are bonded to form a ring; and X⁻ is an anion, and a base to obtain 4-(methylthio)-2-oxo-1-butanol, and reacting the 4-(methylthio)-2-oxo-1-butanol thus obtained with oxygen and a compound represented by the formula (1):

wherein A represents a hydrogen atom or a group represented by R—CH₂—, wherein R is a hydrogen atom or an alkyl group; in the presence of a copper compound to obtain the 2-hydroxy-4-(methylthio)butyrate compound.

13. A process for producing a 2-hydroxy-4-(methylthio) butyrate compound represented by the formula (2):

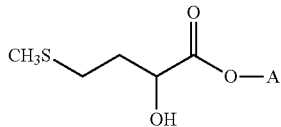 (2)

wherein A is as defined above, which comprises the steps of:

reacting formaldehyde with 3-(methylthio)propionaldehyde in the presence of a triazole compound represented by the formula (4):

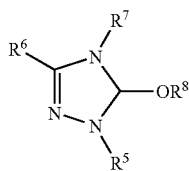 (4)

wherein $R^5$ and $R^6$ are the same or different and each is an optionally substituted alkyl group or an optionally substituted aryl group;

$R^7$ is an optionally substituted alkyl group, an optionally substituted aryl group, an optionally substituted alkenyl group, a halogen atom or a hydrogen atom;

$R^8$ is an optionally substituted alkyl group; and $R^6$ and $R^7$ may be combined together with the carbon atom and the nitrogen atom to which they are bonded to form a ring, to obtain 4-(methylthio)-2-oxo-1-butanol, and reacting the 4-(methylthio)-2-oxo-1-butanol with oxygen and a compound represented by the formula (1):

A-OH (1)

wherein A is a hydrogen atom or a group represented by R—$CH_2$—, wherein R is a hydrogen atom or an alkyl group, in the presence of a copper compound to obtain the 2-hydroxy-4-(methylthio)butyrate compound.

14. The process for producing a 2-hydroxy-4-(methylthio) butyrate compound according to claim 2, wherein the copper compound is a bivalent copper compound.

15. The process for producing a 2-hydroxy-4-(methylthio) butyrate compound according to claim 14, wherein the bivalent copper compound is copper acetate (II), copper (II) acetylacetonate, copper carbonate (II), copper chloride (II), copper sulfate (II), copper hydroxide (II) or copper oxide (II).

16. The process for producing 4-(methylthio)-2-oxo-1-butanol according to claim 7, wherein the base is at least one member selected from the group consisting of a tertiary amine, an alkali metal hydroxide, an alkaline earth metal hydroxide, an alkali metal carbonate, an alkaline earth metal carbonate and an alkali metal bicarbonate.

\* \* \* \* \*